United States Patent [19]
Dawes et al.

[11] 3,973,010
[45] Aug. 3, 1976

[54] INSECTICIDAL AND ACARICIDAL COMPOSITION AND METHOD WITH TRIAZOLYL PHOSPHORIC ESTERS ACID

[75] Inventors: Dag Dawes, Pratteln; Beat Bohner, Binningen, both of Switzerland

[73] Assignee: Ciba-Geigy Corporation, Ardsley, N.Y.

[22] Filed: Jan. 7, 1975

[21] Appl. No.: 539,143

Related U.S. Application Data

[62] Division of Ser. No. 302,691, Nov. 1, 1972, Pat. No. 3,875,179.

[30] Foreign Application Priority Data

Aug. 24, 1972   Switzerland.................. 12541/72

[52] U.S. Cl. ............................................. 424/200
[51] Int. Cl.² ........................................... A01N 9/36
[58] Field of Search ................................... 424/200

[56] References Cited
OTHER PUBLICATIONS
Chem. Abst., vol. 71, 1969, Item 101861 (c) p. 355.

Primary Examiner—Albert T. Meyers
Assistant Examiner—Allen J. Robinson
Attorney, Agent, or Firm—Harry Falber

[57] ABSTRACT

Insecticidal and acaricidal composition and method utilizing triazolyl phosphoric acid esters of the formula

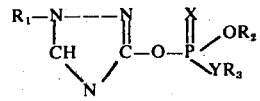

wherein
$R_1$ represents a phenyl group susbstituted by one or more fluorine atoms or lower haloalkyl groups or by at least one chlorine atom and at least one fluorine atom or lower haloalkyl groups, $R_2$ and $R_3$ are each lower alkyl and X and Y are each oxygen or sulphur.

10 Claims, No Drawings

INSECTICIDAL AND ACARICIDAL COMPOSITION AND METHOD WITH TRIAZOLYL PHOSPHORIC ESTERS ACID

This is a divisional of application Ser. No. 302,691, filed on Nov. 1, 1972, now U.S Pat. No. 3,875,179.

The present invention relates to new triazolyl phosphoric acid esters, their manufacture and their use in pest control.

According to the present invention there are provided triazolyl phosphoric acid esters corresponding to the formula

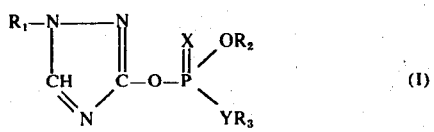

wherein $R_1$ represents a phenyl group substituted by one or more fluorine atoms or lower haloalkyl groups or by at least one chlorine atom and at least one fluorine atom or lower haloalkyl groups, $R_2$ and $R_3$ are each lower alkyl and X and Y are each oxygen or sulphur.

Preferred lower haloalkyl groups are trifluoromethyl and difluorochloromethyl.

Preferred on account of their activity are compounds of formula I wherein $R_1$ is 4-fluorophenyl, 2,3,4,5,6-pentafluorophenyl, 3-chloro-4-fluorophenyl, 2-trifluoromethylphenyl, 3-trifluoromethylphenyl, 4-trifluoromethylphenyl, 3-difluorochloromethylphenyl, 3-chloro-4-trifluoromethylphenyl, 2-chloro-5-trifluoromethylphenyl, 3-trifluoromethyl-4-chlorophenyl, $R_2$ is methyl or ethyl, $R_3$ is methyl, ethyl or propyl, and X and Y are each oxygen or sulphur.

The compounds of formula I may be manufactured by reacting (a) a hydroxytriazole of the formula

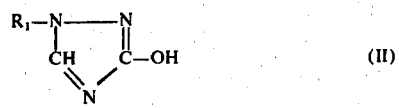

with a phosphoric acid halide of the formula

in the presence of an acid binding agent, or (b) a salt of a hydroxytriazole of formula II with a phosphoric acid halide of formula III.

In formulae II and III the symbols $R_1$ to $R_3$ and X have the meanings given for formula I and Hal stands for fluorine, chlorine, bromine or iodine, especially chlorine or bromine. Suitable salts of hydroxytriazoles of formula II for use in the process according to the invention are for example those of monovalent metals, particularly the alkali metal salts, but others may also be used, for example salts of monovalent heavy metals.

The following bases may be used, for example, as acid binding agents: tertiary amines such as triethylamine, dimethyl aniline, pyridine bases, inorganic bases, such as hydroxides and carbonates of alkali and alkaline earth metals, preferably sodium and potassium carbonate.

The reactions are preferably carried out in a solvent or diluent inert to the reactants. For this, the following are, for example, suitable: aromatic hydrocarbons such as benzene, toluene, petroleum ether, halohydrocarbons, chlorobenzene, polychlorobenzenes, bromobenzene, chlorinated alkanes with 1 to 3 carbon atoms, ethers such as dioxane, tetrahydrofuran; esters such as ethyl acetate; ketones such as methyl ethyl ketone, diethyl ketone, nitriles, etc.

The starting materials of formula II are partly known compounds which can be made by methods known per se. These compounds are obtained, for example, by reacting a correspondingly substituted semicarbazide with orthocarboxylic acid ethyl esters, e.g. alkyl formates, or by first formulating a correspondingly substituted semicarbazide followed by ring closure under alkaline conditions.

In this way, the following novel starting materials of formula II may, for example, be made:

| Structure | Melting point |
|---|---|
| CF$_3$-phenyl | 207 – 209 |
| F-phenyl | > 300 |
| Cl, CF$_3$-phenyl | 273 – 275 |
| pentafluorophenyl | 201 – 204 |

The compounds of formula I have broad spectrum biocidal activity and can be used for combating various vegetable and animal pests, for examples as viricides, selective herbicides and molluscicides.

They are effective above all against all development stages such as eggs, larvae, nymphs, pupae and adults of insects and representatives of the order Acarina such as mites and ticks.

The compounds of formula I can be used for example against the following insects or representatives of the order Acarina: Insects of the families: Teltigonidae, Gryllidae, Gryllotalpidae, Blattidae, Peduviidae, Phyrrhocoriae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymatriidae, Pyralidae, Culicidae, Tipulidae, Stomoxydae, Trypetidae, Muscidae, Calliphoridae and Pulicidae as well as Acarina of the families Ixodidae, Argasidae, Tetranychidae and Dermanyssidae.

The insecticidal and/or acaricidal action can be substantially broadened and matched to given circumstances by the addition of other insecticides and/or acaricides.

As additives, the following active substances are, for example, suitable:

Organic phosphorus compounds

Bis- O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-ethylthio)ethyldithiophosphate (DISULFOTON)
O,O-dimethyl-S-2-(ethylsulphinyl)ethylthiophosphate (OXYDEMETONMETHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4-5-trichlorophenylthiophosphate (RONNEL)
O-ethyl-0,2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-jodphenyl)-thiophosphate (JODOFENPHOS)
4-tert. butyl-2-chlorophenyl-N-methyl-O-methylamidophosphate (CRUFOMATE)
O,O-dimethyl-O-(3-methyl-4-methylmercaptophenyl)-thiophosphate (FENTHION)
Isopropylamino-O-ethyl-O-(4-methylmercapto-3-methylphenyl)-phosphate
O,O-diethyl-O-p-(methylsulphinyl)phenyl-thiophosphate (FENSULFOTHION)
O-p-(dimethylsulphamido)phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethylthiophosphate
Phenylglyoxylonitriloxim-O,O-diethylthiophosphate (PHOXIM)
O,O-diethyl-0-(3-chloro-4-methyl-2-oxo-2-H-1-benzopyran -7-yl)thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(diethoxyphosphinylimino)-1,3-dithiolane
O,O-dimethyl-S-[0,0-dimethyl-S-2-methoxy-1,3,4-thiadiazol -5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphte
O,O,-diethyl-O-2-pyrazinylthiophosphate (THIONAZIN)
O,O-diethyl-O(2-isopropyl-4-methyl-6-pyrimidyl)thiophosphate (DIAZINON)
O,O-diethyl-O-(
O,O-dimethyl-O-(4-oxo-1,2,3-benzotriazine-3(4H)-ylmethyl)-dithiophosphate (AZINPHOSMETHYL)
O,O-diethyl-S-(4-oxo-1,2,3-benzotriazine-3(4H)-ylmethyl)-dithiophosphate (AZINPHOSETHYOL)
S-[(4,6-diamino-s-triazine-2-yl)methyl]O,O-dimethyl-dithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETON-S-METHYL)
2O,O-dimethyl-phosphoryl-thiomethyl)-5-methoxy-pyron-4,3,4-dichlorobenzyl-triphenylphosphoniumchloride
O,O-diethyl-S-(2,5-dichlorophenylthiomethyl)dithiophosphate (PHENKAPTON)
O,O-diethyl-O-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-diethyl-O-[2-diemthylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-diemthyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethyl-thiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)

O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O,2,4-dichlorophenyl-O-methylisopropylamidothiophosphate
O,O-diethyl-O-2,5-dichloro-4-bromophenylthiophosphate (BROMOPHOS-ETHYL)
Dimethyl-p-(methylthio)phenylphosphate
O,O-dimethyl-O-p-sulfamidophenylthiophosphate
O-[p-(p-chlorophenyl)azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
Tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
Dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
Diethyl-S-2-(ethylsulphinyl)ethyl dithiophosphate (OXIDISULFOTON)
Bis-O,O-diethylthiophosphoric acid anhydride (SULFOTEP)
Dimethyl-1,3-di(carbomethoxy)-1-propen-2-yl-phosphate
Dimethyl-(2,2,2-trichloro-1-butyroyloxyethyl)phosphonate (BUTONATE)
O,O-dimethyl-O-(2,2-dichloro-1-methoxy-vinyl)phosphate
Bis-(dimethylamido)fluorphosphate (DIMEFOX)
3,4-dichlorobenzyl-triphenylphosphoniumchloride
Dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
Diisopropylaminofluorophosphate (MIPAFOX)
O,O-dimethyl-S-(morpholinylcarbamoylmethyl)dithiophosphate (MORPHOTHION)
Bismethylamido-phenylphosphate
O,O-dimethyl-S-(benzene sulphonyl)dithiophosphate
O,O-dimethyl-(S and O)-ethylsulphinylethylthiophosphate
O,O-diethyl-O-4-nitrophenylphosphate
Triethoxy-isopropoxy-bis(thiophosphinyl)disulphide
2-methoxy-4H-1,3,2,benzodioxaphosphorin-2-oxide
Octamethylpyrophosphoramide (SCHRADAN)
Bis (dimethoxythiophospphinylsulphido)-phenylmethane
N,N,N',N'-tetramethyldiamidofluorophosphate (DIMEFOX)
O-phenyl-O-p-nitrophenyl-methanthiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethyl-phenyl)-thiophosphate
4,4'-bis-(O,O-dimethylthiophosphoryloxy)-diphenyl disulphide
O,O-di-($\beta$-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-(O,O-dimethylphosphoryl)-6-chloro-bicyclo(3.2.0)-heptadiene (1,5)
O-methyl-O-(2-i-propoxycarbonyl-1-methylvinyl)-ethylamidothiophosphate.

Ritrophenols and derivatives 4,6-dinitro-6-methylphenol, Na-salt [Dinitrocresol]
dinitrobutylphenol-(2,2',2''-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)
6-chloriperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxol, 3-dithiolo-[4,5-b]-quinoxaline [Quinomethionate]
(I)-3-(2-furfuryl)-2-methyl-4-oxocyclopent-2-enyl(I)-(cis+trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]

4-chlorobenzyl-4-fluorophenyl-sulphide [Fluorobenside]
5,6-dichloro-1-phenoxycarbanyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(,5-6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl)-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamate 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-)methyl-carbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methyl-carbamate (CARBOFURAN)
2-methyl-2-methylthio-propionaldehyde-O-(methyl-carbamoyl)-oxime (ALDECARB)
8-chinaldyl-N-methylcarbamate and their salts
methyl 2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methyl-carbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylprazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3-dimethylamino-methyleneiminophenyl-N-methylcarbamate (FORMETANATE) and their salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithioland-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetyl-carbamate
3-isopropylphenyl-N-methyl-N-methylthiomethyl-carbamate
O-(2,2-dimethyl-4-chloro-2,3-dihydro-7-benzofuranyl)-N-methylcarbamate
O-(2,2,4-trimethyl-2,3-dihydro-7-benzofuranyl)-N-methylcarbamate
O-naphthyl-N-methyl-N-acetyl-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate 2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino)-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonalethyl)-3-methyl-5-pyrazolyl-N,N-dimethylcarbamate
3-methyl-4(dimethylamino-methylmercapto-methylencimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
2-[dipropargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γ HCH]
1,2,4,5,6,7,8,8-octachloro-3α,4,7,7α'tetrahydro-4,7-methylenindane [CHLORDAN]
1,4,5,6,7,8,8-heptachloro,3α,4,7,7α-tetrahydro-4,7-methylenindane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-oxtahydro-exo-1,4-endo-5,8-dimethanonaphthalene (DIELDRIN)
1,2,3,4,10,10-hexachloro-5,7-epoxy-1,4,4α,5,6,7,8,8α-octyhydro-endo-endo-5,8-dimethanonaphthalene [ENDRIN]

The active substances of formula I are suitable for combating representatives of the order Thallophyta, such as bacteria and fungi. Especially they possess fungicidal properties against phytopathogenic fungi of the following classes: Oomycetes, Phycomycetes, Ascomycetes, Basidiomycetes, Denteromycetes.

Because of their biocidal properties, the compounds of formula I can be used not only in plant protection but also for disinfecting and protecting various types of material from fungal attack. In this connection, it has proved particularly advantageous that the compounds of formula I generate no poisonous effects in warmblooded animals in the concentrations necessary for disinfection and materials protection.

The compounds of formula I can be formulated in various mixing ratios with known fungicides and microbicides, whereby mixtures of compounds arise with advantages compared to the individual components. The following known fungicides are, for example, suitable for formulating with the active substances of formula I:
dodecylguanidine acetate (DODINE)
pentachloronitrobenzene (QUINTOZENE)
pentachlorophenol (PCP)
2-(1-methyl-n-propyl)-4,6-dinitrophenyl-2-methyl-crotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPAT)
N-(trichloromethylthio) cyclohex-4-en-1,2-dicarboximide (CAPTAN)
N-(1,1,2,2-tetrachloroethylthio)cyclohex-4-en-1,2-dicarboximide (CAPTAFOL)
N-methansulfonal-N-trichloromethylthio-chloroaniline
N'-dichlorofluoromethylthio-N,N-dimethyl-N'-phenyl-sulfamide (DICHLOFLUANID)
O-ethyl-S-benzyl-phenyldithiophosphate
O,O-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric) (MANEB)
tetramethylthiuramdisulfide (THIRAM)
1-oxy-3-acetyl-6-methyl-cyclohexene-(5)dione-(2,4) (DEHYDROACETIC ACID)
8-hydroxyquinoline (8-QUINOLINOL)
2-dimethylamino-6-methyl-5-n-butyl-4-hydroxy-pyrimidine
methyl-N-benzimidazole-2-yl-N-(butylcarbamoyl)carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazin-2-thione (DAZOMET)
2,3-dihydro-5-carboxanilido-6-methyl-1,4-oxathine
pentachlorobenzyl alcohol.

Additionally, the new compounds of formula I possess nematocidal properties, and can be used, for example, to combat the following plant parasitic nematodes: Meloidogyne sp., Heterodera sp., Ditylenchus sp., Pratylenchus sp., Paratylenchus sp., Anguina sp., Helicotylenchus sp., Tylenchorhynchus sp., Rotylenchulus sp., *Tylenchulus semipenetrans, Radopholus similus*, Belonolaimus sp., Trichodorus sp., Longidorus sp., Aphelenchoides sp., Xiphinema sp.

The compounds of the formula I may be used as pure active substance or together with suitable carriers and/or additives. Suitable carriers and additives can be solid or liquid and correspond to the substances conventionally used in formulation technique such, for example, as solvents dispersants, wetting agents, adhesives, thickeners, binders and/or fertilisers.

For application, the compounds of the formula I may be processed to dusts, emulsion concentrates, granules, dispersions, sprays, to solutions, or suspensions in the conventional formulation which is commonly employed in application terminology. Mention may also be made of "cattle dips" and "spray races", in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may be available and can be used in the following forms:

Solid forms

Dusts, tracking agents, granules, coated granules, impregnated granules and homogeneous granules.

Liquid forms:
 a. active substance concentrates dispersible in water: wettable powders, pastes, emulsions;
 b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaccous earth, precipitated silica, alkaline earth silicates, sodium and potassium aluminum silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives and the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilize the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene acid, fatty alcohol sulfates such as salts of sulfated hexadecanols, heptadecanols, octadecanols, and salts of sulfated fatty alcohol glycol ethers, the sodium salt of oleyl methyl tauride, ditertiary ethylene glycols, dialkyl dilauryl ammonium chloride and fatty acid alkali and alkaline earth metal salts.

Suitable anti-foam agents are silicone oils.

The active substances are mixed, ground, sieved and strained with the additives mentioned above that, in wettable powder, the solid particle size of from 0.02 to 0.04 and in pasts, of 0.03 mm is not exceeded. To produce emulsifiable concentrates and pastes, dispersing agents such as those cited above, organic solvents and water are used. Examples of suitable solvents are the following: alcohols, benzene, xylenes, toluene, dimethyl sulfoxide, and mineral oil fractions boiling between 120° and 350° C. The solvents must be practically odourless not phytotoxic, inert to the active substances.

Furthermore, the agents according to the invention can be applied in the form of solutions. For this purpose the active substance or several active substances of the general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be used as organic solvents.

The content of active substance in the above described agents is between 0.1% to 95%, in which connection it should be mentioned that in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:
 a.
 5 parts of active substance
 95 parts of talcum
 b.
 2 parts of active substance
 1 part of highly disperse silica
 97 parts of talcum.

The active substances are mixed with the carriers and ground.

Granules

The following substances are used to produce 5% granules:
5 parts of active substance
0.25 parts of epichlorohydrin
0.25 parts of cetyl polyglycol ether
3.50 parts of polyethylene glycol
91 parts of kaolin (particle size 0.3-0.8 mm).

The active substance is mixed with epichlorohydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder

The following constituents are used for the preparation of (a) a 40%, (b) and (c) a 25%, and (d) a 10% wettable powder:

a.
40 parts of active substance
5 parts of sodium lignin sulphonate
1 part of sodium dibutyl-naphthalene sulphonate
54 parts of silica acid.

b.
25 parts of active substance
4.5 parts of calcium lignin sulphonate
1.9 parts of Champagne chalk/hydroxyethyl cellulose mixture (1:1)
1.5 parts of sodium dibutyl naphthalene sulphate
19.5 parts of silica acid
19.5 parts of Champagne chalk
28.1 parts of kaolin.

c.
25 parts of active substance
2.5 parts of isooctylphenoxy-polyoxyethylene-ethanol
1.7 parts of Champagne chalk/hydroxyethyl cellulose mixture (1:1)
8.3 parts of sodium aluminium silicate
16.5 parts of kieselgur
46 parts of kaolin.

d.
10 parts of active substance
5 parts of naphthalenesulphonic acid/formaldehyde condensate
82 parts of kaolin.

The active substances are intimately mixed, in suitable mixers, with the additives, the mixture being then ground in the appropriate mills and rollers. Wettable powder are obtained which can be diluted with water to give suspensions of any desired concentration.

Emulsifiable concentrates

The following substances are used to produce (a) a 10% and (b) a 25% emulsifiable concentrate:

a.
10 parts of active substance
3.4 parts of epoxidised vegetable oil
13.4 parts of a combination emulsifier consisting of fatty alcohol polyglycol ether and alkylarylsulphonate calcium salt
40 parts of dimethylformamide
43.2 parts of xylene.

b.
25 parts of active substance
2.5 parts of epoxidised vegetable oil
10 parts of an alkylarylsulphonate/fatty alcoholpolyglycol ether mixture
5 parts of dimethylformamide
57-5 parts of xylene.

From these concentrates it is possible to produce, by dilution with water, emulsion of any desired concentration.

Spray

The following constituents are used to prepare a 5% spray:
5 parts of active substance
1 part of epichlorohydrin
94 parts of benzine (boiling limits 160°-190°C).

The following examples will serve to illustrate the preparation of compounds according to the invention and their properties:

EXAMPLE 1

O,O-diethyl-O-[1-(3-trifluoromethylphenyl)-1,2,4-triazolyl-(3)]-thiophosphate a. 23.9 g 1-(3-trifluoromethylphenyl)-semicarbazide and 14.8.g orthoformic acid ester were heated together with 40 ml glycol monomethyl ether whereon a clear yellow solution was obtained. The ethanol forming at an internal temperature of 120°C was continuously distilled off. After 4½ hours the mixture was allowed to cool and treated with 200 ml ether. The compound of the formula

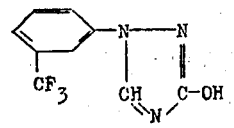

was obtained, having a decomposition point of 210°C.

b. 40 g 1-(3-trifluoromethylphenyl)-3-hydroxy-1,2,4-triazole and 23.6 g potash were heated for 1 hour under reflux together with a spatula point of copperbronze in 400 ml methyl ethyl ketone. Then 32.2 g O,O-diethyl thiophosphoric acid chloride were added dropwise at 50°C. After three hours heating under reflux, the solvent was evaporated in vacuo. The residue was taken up in ether and washed successively with water, 0.5N HCl, saturated bicarbonate solution and brine. After drying over sodium sulphate the ether was evaporated in vacuo to leave the crude product. By filtration through 800 g silica gel with methylene chloride as solvent, the compound of the formula

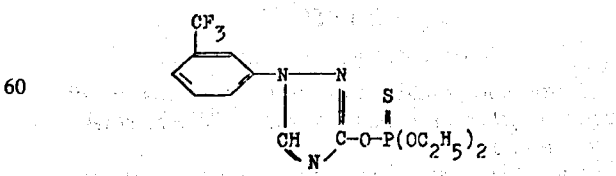

is obtained. M.Pt.: 37°-39°C.

The following compounds were also made in analogous fashion:

$$R_1-N-N \atop CH \quad C-O-P(=S)(OR_2)(YR_3) \atop N$$

| R₁ | R₂ | R₃ | Y | |
|---|---|---|---|---|
| 2-CF₃-phenyl | C₂H₅ | C₂H₅ | O | M.Pt.: 59–60°C |
| 3-CF₃-phenyl | C₂H₅ | (n)C₃H₇ | S | $n_D^{20} = 1.5421$ |
| 3-CF₃-4-Cl-phenyl | C₂H₅ | C₂H₅ | O | M.Pt.: 57–59°C |
| 4-F-phenyl | C₂H₅ | C₂H₅ | O | M.Pt.: 51–53°C |
| 2,3,4,5,6-pentafluorophenyl | C₂H₅ | C₂H₅ | O | $n_D^{20} = 1.4926$ |
| 2-CF₃-phenyl | C₂H₅ | (n)C₃H₇ | S | |
| 3-CF₃-4-Cl-phenyl | C₂H₅ | C₂H₅ | O | |
| 3-CF₃-4-Cl-phenyl | C₂H₅ | C₂H₅ | O | |
| 3-CF₂Cl-phenyl | C₂H₅ | C₂H₅ | O | |
| 3-F-4-Cl-phenyl | C₂H₅ | C₂H₅ | O | |
| 3-CF₃-phenyl | CH₃ | CH₃ | O | |
| 2-CF₃-phenyl | CH₃ | CH₃ | O | |
| 4-F-phenyl | C₂H₅ | (n)C₃H₇ | S | |

EXAMPLE 2

Insecticidal ingest poison action

Cotton and potato plants are sprayed with a 0.05% aqueous emulsion (obtained from a 10% emulsifiable concentrate).

After the coating has dried, *Disdercus fasciatus* nymphs are settled on the cotton plants and Colorado potato beetle larvae (*Leptinotarsa decemlineata*) on the potato plants. The test is carried out at 24°C and 60% relative humidity. In the above test the compounds according to Example 1 displayed good ingest poison action against *Disdercus fasciatus* and *Leptinotarsa decemlineata*.

EXAMPLE 3

Acaricidal action a. Action on mites (*Tetranychus urticae*)

For testing the acaricidal action bean leaves infested with adults, rest stages and eggs of the red spidermite (*Tetranychus urticae*), were treated with a 0.05% aqueous emulsion of the substance to be tested (made from a 25% emulsifiable concentrate). The test was evaluated after 6 days. Phosphoric acid ester resistant strains of red spidermite were used as test animals.

b. Action on ticks (*Boophilus microplus*) and their development stages

For the following test in each case 10 adult ovipositing ticks were dipped for three minutes in aqueous emulsions of active substance (Concentrations: 800; 400; 200; 100; 50; 10 and 1 ppm).

The ticks were then kept at 27°C and 80% relative humidity. Egglaying was determined at the 5th, 10th and 15th day.

The compounds according to example 1 tested according to the above tests (a) and (b) showed good action against *Tetranychus urticae* and *Boophilus microplus*.

Action against soil nematodes

To test the action against soil nematodes, the active substance (in the concentration indicated in each case is applied to and intimately mixed with soil infected with root gall nematodes (*Meloidgyne avenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing respectively. The compounds according to Example I display good action against *Meloidgyne avenaria* is this test.

What we claim is:

1. An insecticidal or acaricidal composition comprising an insecticidally or acaricidally effective amount of a compound of the formula

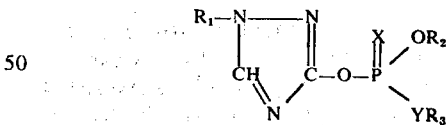

wherein R₁ represents phenyl substituted by one to five fluorines or halo-lower alkyls, or by one chlorine and one substituent selected from the group consisting of fluorine and halo-lower alkyl; R₂ and R₃ are each lower alkyl; and X and Y are each oxygen or sulfur; together with a suitable carrier therefor.

2. The composition of claim 1, wherein R₁ is 4-fluorophenyl, 2,3,4,5,6-pentafluorophenyl, 3-chloro-4-fluorophenyl, 2-trifluoromethylphenyl, 3-trifluoromethylphenyl, 4-trifluoromethylphenyl, 3-difluorochloromethylphenyl, 3-chloro-4-trifluoromethylphenyl, 2-chloro-5-trifluoromethylphenyl or 3-trifluoromethyl-4-chlorophenyl, R₂ is methyl or ethyl, R₃ is methyl, ethyl or propyl, and X and Y are each oxygen or sulphur.

3. The composition of claim 2, wherein said compound is

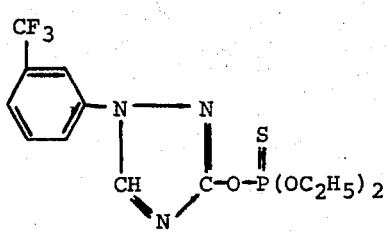

4. The composition of claim 2, wherein said compound is

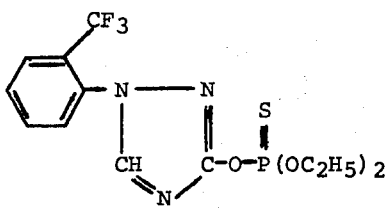

5. The composition of claim 2, wherein said compound is

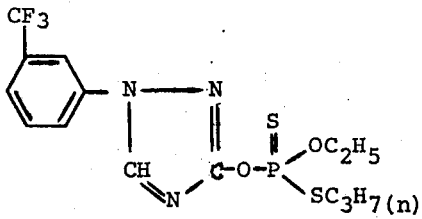

6. The composition of claim 2, wherein said compound is

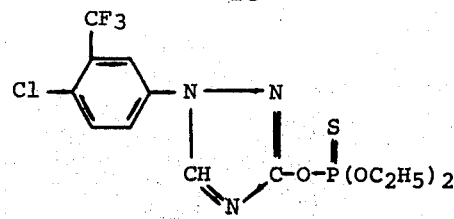

7. The composition of claim 2, wherein said compound is

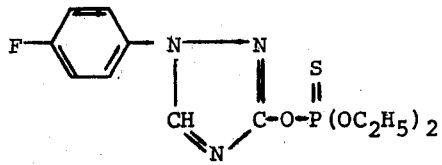

8. The composition of claim 2, wherein said compound is

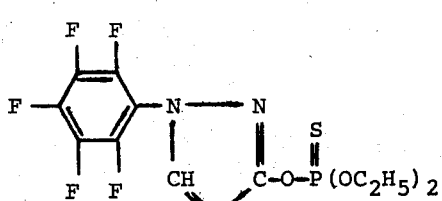

9. A method for combatting insects or acaride which comprises applying to the locus thereof an insecticidally or acaricidally effective amount of a compound of the formula of claim 1.

10. The method of claim 9, wherein $R_1$ is 4-fluorophenyl, 2,3,4,5,6-pentafluorophenyl, 3-chloro-4-fluorophenyl, 2-trifluoromethylphenyl, 3-trifluoromethylphenyl, 4-trifluoromethylphenyl, 3-difluorochloromethylphenyl, 3-chloro-4-trifluoromethylphenyl, 2-chloro-5-trifluoromethylphenyl or 3-trifluoromethylphenyl-4-chlorophenyl, $R_2$ is methyl or ethyl, $R_3$ is methyl, ethyl or propyl, and X and Y are each oxygen or sulphur.

* * * * *